United States Patent [19]

Kawajiri et al.

[11] Patent Number: 5,719,318
[45] Date of Patent: Feb. 17, 1998

[54] PROCESS FOR PRODUCTION OF ACRYLIC ACID

[75] Inventors: Tatsuya Kawajiri; Michio Tanimoto; Daisuke Nakamura, all of Himeji, Japan

[73] Assignee: Nippon Shokubai Co., Ltd., Osaka, Japan

[21] Appl. No.: 810,923

[22] Filed: Mar. 5, 1997

[30] Foreign Application Priority Data

Mar. 6, 1996 [JP] Japan ................... 8-048562

[51] Int. Cl.$^6$ ................... C07C 51/16; C07C 51/235
[52] U.S. Cl. ................... 562/532; 562/534; 562/535
[58] Field of Search ................... 562/532, 534, 562/535

[56] References Cited

U.S. PATENT DOCUMENTS

| | | | |
|---|---|---|---|
| 4,051,180 | 9/1977 | Shaw et al. | 260/530 N |
| 4,157,987 | 6/1979 | Dolhyj et al. | 252/437 |
| 4,333,858 | 6/1982 | Decker et al. | 252/455 R |
| 4,892,856 | 1/1990 | Kawajiri et al. | 502/247 |
| 5,177,260 | 1/1993 | Kawajiri et al. | 562/535 |
| 5,206,431 | 4/1993 | Hashiba et al. | 562/534 |
| 5,472,928 | 12/1995 | Scheuerman et al. | 502/305 |

FOREIGN PATENT DOCUMENTS

| | | |
|---|---|---|
| 0146099 | 6/1985 | European Pat. Off. . |
| 0427508 | 5/1991 | European Pat. Off. . |
| 0450596 | 10/1991 | European Pat. Off. . |
| 0758562 | 2/1997 | European Pat. Off. . |
| 1374291 | 11/1974 | United Kingdom . |

Primary Examiner—Gary Geist
Assistant Examiner—Rosalynd A. Keys
Attorney, Agent, or Firm—Sherman and Shalloway

[57] ABSTRACT

As an improvement for the process for production of acrylic acid by subjecting acrolein or an acrolein-containing gas to gas-phase oxidation with molecular oxygen in a fixed bed multitubular reactor, there is provided a novel process capable of producing acrylic acid at a high yield by suppressing the generation of heat spots in catalyst or the build-up of heat in hot spots of catalyst. The process comprises filling, in each of reactor tubes, two or more kinds of catalyst particles of different volumes so as to form a plurality of catalyst layers in the axial direction of the tube in such a manner that the particle volume of catalyst layer becomes smaller as the position of catalyst layer changes from the raw material gas inlet side of the tube to the raw material gas outlet side, each catalyst particle comprising, as the active component, a compound oxide containing at least Mo and V.

2 Claims, No Drawings

PROCESS FOR PRODUCTION OF ACRYLIC ACID

The present invention relates to a process for production of acrylic acid by subjecting acrolein or an acrolein-containing gas to gas-phase catalytic oxidation with molecular oxygen or a molecular oxygen-containing gas in a fixed bed multi tubular reactor.

For the process for production of acrylic acid by subjecting acrolein to gas-phase catalytic oxidation, or for the catalyst used therein, many proposals were made in, for example, Japanese Patent Publication No. 26287/1969, Japanese Patent Application Kokai (Laid-Open) No. 8360/1972, Japanese Patent Publication No. 43917/1978 and Japanese Patent Application Kokai (Laid-Open) No. 218334/1991. Some of the catalysts proposed in these literatures can produce acrylic acid at a fairly high yield viewed from the industrial standpoint, and some of them are in actual use in acrylic acid production by direct oxidation of propylene. In industrial production of acrylic acid with these catalysts, however, there are various problems. One of the problems is generation of high-temperature portions (hereinafter referred to as hot spots) in catalyst layer. In industry, it is required to increase the productivity of acrylic acid and, to achieve it, increased concentration or increased space velocity of reaction gas (raw material) is employed generally. The increased acrolein concentration is advantageous in plant and equipment investment and operating cost (e.g. electric power expense) but has the following problems. That is, the heat of reaction generated is larger; it generates hot spots in the catalyst layer and gives rise to excessive oxidation; as a result, the catalyst used is thermally deteriorated and, in the worst case, run-away may be brought about.

Hence, prior arts were made in order to keep the temperatures of hot spots lower. For example, Japanese Patent Publication No. 30688/1978 describes an approach that the catalyst portion filled at the raw material gas inlet side of reactor tube is diluted with an inert substance; and Japanese Patent Publication No. 10802/1995 proposes an approach that the proportion of catalyst active Component supported on carrier is made larger as the position of catalyst layer changes from the raw material gas inlet side of reactor tube to the raw material gas outlet side. However, in the former approach, the inert substance as diluent should be uniformly mixed with said catalyst portion, requiring much effort and, moreover, it is difficult to fill a uniform mixture into a reactor tube; thus, the approach is not satisfactory. Meanwhile, in the latter approach, production of catalysts is complicated and sufficient care must be taken to fill a plurality of catalysts in a right order.

Therefore, the object of the present invention lies in solving the problems of the prior art and providing a process for producing acrylic acid efficiently by subjecting acrolein or an acrolein-containing gas to gas-phase catalytic oxidation with molecular oxygen or a molecular-oxygen-containing gas.

More particularly, the object of the present invention lies in providing a process for producing acrylic acid by subjecting acrolein or an acrolein-containing gas to gas-phase catalytic oxidation with molecular oxygen or a molecular-oxygen-containing gas, in which process the generation of hot spots or the build-up of heat in hot spots is suppressed even under the high-load reaction conditions and consequently acrylic acid can be produced at a high productivity and, moreover, catalyst life can be extended.

Up to the completion of the present invention, it had been considered that in the exothermic reaction such as catalytic gas-phase oxidation conducted in the present invention, use of catalyst particles of larger size hinders heat transfer between catalyst particles and as a result the temperature of hot spots becomes higher. The present inventors, however, found out that use of catalyst particles of larger size, i.e. larger volume, can lower the temperature of hot spots and further that when two or more kinds of catalyst particles of different volumes are filled in a reactor tube so as to form a plurality of catalyst layers (reaction zones) in the axial direction of the tube in such a manner that the volume of catalyst particle becomes smaller as the position of catalyst layer changes from the raw material gas inlet side of the tube to the raw material gas outlet side, the above-mentioned object of the present invention can be attained.

According to the present invention there is provided a process for producing acrylic acid by subjecting acrolein or an acrolein-containing gas to gas-phase catalytic oxidation with molecular oxygen or a molecular oxygen-containing gas in a fixed bed multi-tubular reactor, in which process two or more kinds of catalyst particles of different volumes are filled in each reactor tube so as to form a plurality of catalyst layers in the axial direction of the tube in such a manner that the volume of catalyst particle becomes smaller as the position of catalyst layer changes from the raw material gas inlet side of the tube to the raw material gas outlet side, each catalyst particle comprising, as the active component, a compound oxide represented by the following general formula:

$$Mo_aV_bW_cA_dB_eC_fD_gO_h$$

wherein Mo is molybdenum; V is vanadium; W is tungsten; A is at least one element selected from antimony and tin; B is at least one element selected form copper and iron; C is at least one element selected from magnesium, calcium, strontium and barium; D is at least one element selected from titanium, zirconium and cerium; and O is oxygen; a, b, c, d, e, f, g and h represent the atom numbers of Mo, V, W, A, B, C, D and O, respectively; and when a is 12, $2 \leq b \leq 14$, $0 \leq c \leq 12$, $0 \leq d \leq 5$, $0 < e \leq 6$, $0 \leq f \leq 3$, $0 \leq g \leq 10$, and h is a value determined by the oxidation states of the elements other than oxygen.

The starting material used in the present invention is acrolein or an acrolein-containing gas. As the acrolein or acrolein-containing gas, there can be used, for example, (1) an acrolein-containing gas obtained by catalytic gas-phase oxidation of propylene and (2) acrolein separated from said gas, which may contain, as necessary, oxygen, steam and/or other gases.

The active component contained in the catalyst particles used in the present invention is a compound oxide represented by the above-mentioned general formula, preferably a compound oxide of the general formula wherein when a is 12, $3 \leq b \leq 10$, $0.1 \leq c \leq 10$, $0 \leq d \leq 4$, $0.1 \leq e \leq 5$, $0 \leq f \leq 2.5$ and $0 \leq g \leq 8$ (h is a value determined by the oxidation states of the elements Mo, V, W, A, B, C and D).

The catalyst particles used in the present invention can be produced by any of various processes ordinarily used in production of such catalyst particles. The starting materials used in production of the catalyst particles are not particularly restricted and can be the ordinarily used ammonium salts, nitrates, sulfates, hydroxides, oxides, etc. of Mo, V, W, A, B, C and D. Compounds each containing different kinds of metals may be used. The catalyst particles of active component-on-inert carrier type can also be used. Specific examples of the carrier used are α-alumina, silicon carbide, silica, pumice, silica-magnesia zirconium oxide, titanium oxide, and silica-alumina. As to the heat-treatment temperature employed in catalyst particles production (i.e. firing temperature), there is no particular restriction. The heat-treatment temperatures of the catalyst particles filled in different catalyst layers (reaction zones) may be the same or different. In the present invention, however, generation of hot spots or heat build-up in hot spots can be suppressed effectively by filling, in the catalyst layer (reaction zone) closest to the raw material gas inlet of each reactor tube, catalyst particles heat-treated at a temperature higher by 5°–30° C., preferably 10°–20° C. than that of the catalyst particles filled in the following catalyst layer downstream of the above catalyst layer.

As to the shape of the catalyst particles, there is no particular restriction. The shape may be any of spherical shape, columnar (pellet-like) shape, ring shape, indefinite shape, etc. The spherical shape need not be a truly spherical shape and may be a substantially spherical shape. The same applies to the columnar shape and the ring shape. As to the dimension (size) of each catalyst particle, the ratio (D/d) of the inner diameter (D) of each reactor tube (in which each catalyst particle is filled) to the diameter (d) of each catalyst particle is desirably 2/1 to 15/1, preferably 2.5/1 to 10/1. Herein, the diameter of catalyst particle refers to diameter of particle (in the case of spherical catalyst particle), diameter of column (in the case of columnar or ring-shaped catalyst particle), or longest distance of arbitrarily selected two ends (in the case of catalyst particle of any other shape). In the columnar or ring-shaped catalyst particle, it is preferable to select the particle length so as to have a particle length/particle diameter ratio of 0.3/1 to 3/1, for the productional or application reasons. The inner diameter (D) of each reactor tube used is desirably 10–50 mm, preferably 15–40 mm. Use of catalyst particles having a larger diameter (d) in the above-mentioned range of D/d gives a smaller pressure resistance in catalyst layer and thereby an energy necessary for introduction of raw material gas into reactor tube can be made smaller.

In the present invention, there is used a fixed bed multi tubular reactor wherein each reactor tube has a plurality of catalyst layers (reaction zones) in the axial direction of the tube. The number of the catalyst layers is appropriately determined so that the highest effect can be obtained. Too large a number produces disadvantages such as complexity of catalyst filling and the like; therefore, an industrially desirable number is about 2–6.

In the present invention, there are prepared two or more kinds of catalyst particles of different volumes, whose active component is a compound oxide represented by the above-mentioned general formula. These catalyst particles are filled in each reactor tube so as to form a plurality of catalyst layers (reaction zones) in the axial direction of the tube in such a manner that the volume of catalyst particle becomes smaller as the position of catalyst layer changes from the raw material gas inlet side of the tube to the raw material gas outlet side. That is, in the present invention, in each reactor tube, a catalyst layer filled with catalyst particles of largest volume must be formed closest to the raw material gas inlet and a catalyst layer filled with catalyst particles of smallest volume must be formed closest to the raw material gas outlet and, as the position of catalyst layer changes from the raw material gas inlet side to the raw material gas outlet side, the volume of catalyst particle must become smaller.

In the present invention, the volume of catalyst particle refers to an average of the volumes of the catalyst particles filled in one catalyst layer (reaction zone). It is, for convenience, an average of the volumes of ten catalyst particles arbitrarily selected from the catalyst particles filled in one catalyst layer. In the case of hollow catalyst particles, e.g. ring-shaped catalyst particles, the volume occupied by the contour of particle is the volume of catalyst particle according to the present invention. In the case of spherical or columnar catalyst particles, the volume of catalyst particle can be determined by ordinary calculation. When the catalyst particle is a molded catalyst obtained by molding an active component into a definite or indefinite shape, the volume of the molded catalyst is the volume of catalyst particle according to the present invention. When the catalyst particle is a supported catalyst comprising an active component and a carrier supporting the active component, the volume of the supported catalyst is the volume of catalyst particle according to the present invention.

In the present invention, it is desirable that the catalyst particles filled in one catalyst layer (reaction zone) have substantially the same volume. Therefore, when catalyst particles having substantially the same volume are filled in one catalyst layer, the volume of catalyst particle or average volume of catalyst particles in one catalyst layer can be expressed by the volume of any one catalyst particle used in the catalyst layer.

In the present invention, it is also desirable that the ratio of the volume of catalyst particle in one catalyst layer (reaction zone) to the volume of catalyst particle in the following catalyst layer downstream of the former catalyst layer is controlled to be 1.2/1 to 27/1, preferably 1.5/1 to 24/1, for the prevention of heat build-up in hot spots as well as for effective reaction. When the volume ratio is smaller than 1.2/1, the effect of using two or more kinds of catalyst particles of different volumes is insufficient; in order to obtain a sufficient effect with such a volume ratio, the number of catalyst layers must be larger, making it necessary to prepare catalyst particles of more kinds different in size and requiring larger labor for filling of catalyst particles. Meanwhile, when the volume ratio is larger than 27/1, the effect of using two or more kinds of catalyst particles of different volumes is insufficient, either; consequently, there arise inconveniences, for example, the length of the catalyst layer closest to the raw material gas inlet of reactor tube becomes very long, or the catalyst particles in the catalyst layer closest to the raw material gas outlet of reactor tube become very small, making large the pressure resistance in catalyst layer.

The length of each of the catalyst layers (reaction zones) formed in each reactor tube in the axial direction of the tube can be appropriately determined so that the catalyst particles produced as mentioned above can exhibit the effect to the maximum extent. The length of the catalyst layer (wherein the catalyst particles of largest volume) closest to the raw material gas inlet of reactor tube is generally 10–80%, preferably 15–70% of the total length of all catalyst layers.

In the present invention, two or more kinds of catalyst particles of different volumes filled in a plurality of catalyst layers (reaction zones) may contain the same or different active components. Even when different active components are contained in different kinds of catalyst particles, the temperature of hot spots can be kept lower by using two or more kinds of catalyst particles of different volumes, whereby the effect of the present invention can be obtained. It is, however, preferable that the catalyst particles filled in one catalyst layer have the same composition (contain the same active component), in view of the uniformity of catalytic activity, the operability of catalyst, etc. Therefore, it is preferable that the catalyst particles of same composition and substantially same volume are filled in one catalyst layer.

In the present invention, the catalyst particles filled in each catalyst layer (reaction zone) may be any of a molded catalyst obtained by moldling an active component into a desired shape, a supported catalyst obtained by supporting an active component on an inert carrier having a desired shape, and a combination of the molded catalyst and the supported catalyst. The shapes of the catalyst particles filled in each catalyst layer may be the same or different; however, the catalyst particles filled in one catalyst layer are preferably molded catalyst particles and/or supported catalyst particles of same shape. When supported catalyst particles are used, the proportions of supported active components in different catalyst layers may be the same or different; however, use of the same proportion of supported active component in all catalyst layers is generally advantageous from the standpoints of catalyst production and catalyst life.

As stated above, in the present invention, generation of hot spots or heat build-up in hot spots can be suppressed by filling, in each of the reactor tubes, two or more kinds of catalyst particles of different volumes each made of a compound oxide represented by the above-mentioned general formula, so as to form a plurality of catalyst layers in the axial direction of the tube in such a manner that the volume of catalyst particle becomes smaller as the position of catalyst layer changes from the raw material gas inlet side of the tube to the raw material gas outlet side; as a result, the reaction of acrylic acid production can be continued over a long period of time without reducing the yield of acrylic acid (an intended product).

Further in the present invention, the pressure loss in catalyst layers can be made smaller than in the conventional process employing catalyst dilution or other measures, by effectively using the catalyst particles of large diameter (i.e. D/d=2/1 to 15/1); as a result, energy saving (e.g. reduced electric power expense of blower) can be achieved.

Furthermore in the present invention, the temperature of hot spots in catalyst layers can be kept lower and the reaction can be conducted more uniformly in all catalyst layers; as a result, there is no local deterioration or damage of catalyst and an extended catalyst life is obtained.

The present invention is hereinafter described with reference to Examples. However, the present invention is in no way restricted to these Examples.

In the Examples, "acrolein conversion (mole %)" and "acrylic acid yield (mole %)" were determined from the following formulae.

Acrolein conversion (mole %)=(moles of acrolein reacted)÷(moles of acrolein fed)×100

Acrylic acid yield (mole %)=(moles of acrylic acid formed)÷(moles of acrolein fed)×100

EXAMPLE 1

In 3,000 ml of water being stirred with heating, 1,014 g of ammonium paramolybdate and 224 g of ammonium metavanadate were dissolved. Separately, in 6,000 ml of water being stirred with heating, 231 g of copper nitrate, 323 g of ammonium paratungstate and 20 g of strontium nitrate were dissolved. The resulting two solutions were mixed and thoroughly stirred with heating and then dried at 120° C. The resulting dried solid was ground into about 100 mesh. The resulting powder was molded, by a tablet machine, into rings of 10 mm (outer diameter)×2 mm (inner diameter)×10 mm (height) and rings of 5 mm (outer diameter)×2 mm (inner diameter)×5 mm (height). The two kinds of rings were heat-treated at 400° C. for 6 hours in an air current to obtain a catalyst 1 (rings of 10 mm in outer diameter) and a catalyst 2 (rings of 5 mm in outer diameter). These catalysts had the following metal composition when oxygen was excluded.

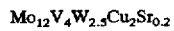

$Mo_{12}V_4W_{2.5}Cu_2Sr_{0.2}$

These catalysts were filled in a stainless steel-made reactor tube of 25 mm in inner diameter, heated in a molten nitrate bath, in such a manner that the catalyst 1 was closer to the raw material gas inlet of the tube and formed a layer of 1,000-mm length and the catalyst 2 was downstream of the catalyst 1 and formed a layer of 2,000-mm length. Then, into the tube was introduced a raw material gas having the following composition, at a space velocity (SV) of 2,000 $hr^{-1}$.

| | |
|---|---|
| Acrolein | 8% by volume |
| Oxygen | 10% by volume |
| Steam | 44% by volume |
| Inert gas (e.g. nitrogen) | 40% by volume |

A reaction started without any abnormality such as run-away or the like and proceeded stably for 8000 hours.

The shapes, volumes and volume ratio of the catalysts 1 and 2 used in the reaction are shown in Table 1, and the results of the reaction are shown in Table 2. Incidentally, the temperature of the nitrate bath used was changed depending upon the reaction time.

EXAMPLE 2

In 3,000 ml of water being stirred with heating, 1,014 g of ammonium paramolybdate and 224 g of ammonium metavanadate were dissolved. Separately, in 6,000 ml of water being stirred with heating, 231 g of copper nitrate, 323 g of ammonium paratungstate and 20 g of strontium nitrate were dissolved. The resulting two solutions were mixed and placed in a ceramic evaporator containing 2,500 g of a spherical carrier made of α-alumina having a surface area of 1 $m^2/g$ or less and an average diameter of 8 mm. The evaporator was placed on a hot water bath and the evaporator contents were evaporated to dryness with stirring, to adhere the catalyst components on the carrier. Then, the carrier-supported catalyst components were heat-treated at 400° C. for 6 hours in an air current to obtain a catalyst 3. A catalyst 4 was obtained in the same manner as above except that the carrier was changed to a spherical carrier having an average diameter of 5 mm.

These catalyst had the same metal composition with catalyst 1 when oxygen and carrier were excluded.

An oxidation reaction was conducted in the same manner as in Example 1 except that the catalysts 3 and 4 were used in place of the catalysts 1 and 2. The shapes, volumes and volume ratio of the catalysts 3 and 4 used in the reaction are shown in Table 1. The results of the reaction are shown in Table 2.

TABLE 1

| Example | Kind of catalyst | Shape of catalyst | Volume of catalyst (mm³/particle) | Volume ratio of catalysts* |
|---|---|---|---|---|
| 1 | Catalyst 1 | Ring | 785.4 | 8.0/1 |
|   | Catalyst 2 | Ring | 98.2 | — |
| 2 | Catalyst 3 | Spherical | 268.1 | 4.0/1 |
|   | Catalyst 4 | Spherical | 65.5 | — |
| 3 | Catalyst 5 | Ring | 169.7 | 1.7/1 |
|   | Catalyst 6 | Ring | 98.2 | — |
| 4 | Catalyst 7 | Ring | 1357.2 | 3.4/1 |
|   | Catalyst 8 | Ring | 402.1 | 4.1/1 |
| 5 | Catalyst | Spherical | 523.6 | 23.3/1 |

TABLE 1-continued

| Example | Kind of catalyst | Shape of catalyst | Volume of catalyst (mm³/particle) | Volume ratio of catalysts* |
|---|---|---|---|---|
| | 10 Catalyst 11 | Spherical | 22.5 | — |

*The ratio of the volume of catalyst particle filled in one catalyst layer to the volume of catalyst particle filled in the following catalyst layer downstream of the former catalyst layer.

TABLE 2

| Example | Reaction time (hr) | Temp. of nitrate bath (°C.) | Maximum temperatures of catalyst layers (°C.) | | | Acrolein conversion (mole %) | Acrylic acid yield (mole %) |
|---|---|---|---|---|---|---|---|
| | | | 1st layer | 2nd layer | 3rd layer | | |
| 1 | Initial | 250 | 308 | 305 | — | 99.3 | 94.0 |
| | 2,000 | 252 | 307 | 305 | — | 99.4 | 94.1 |
| | 8,000 | 255 | 311 | 309 | — | 99.5 | 94.0 |
| 2 | Initial | 245 | 310 | 298 | — | 99.4 | 94.0 |
| | 2,000 | 246 | 308 | 300 | — | 99.3 | 93.9 |
| | 8,000 | 249 | 311 | 302 | — | 99.5 | 94.2 |

1st layer is a catalyst layer closest to the raw material gas inlet of the reactor tube; 2nd layer is a catalyst layer downstream of the 1st layer; and 3rd layer is a catalyst layer downstream of the 2nd layer. This applies also to Table 3 and Table 4.

Comparative Example 1

A reaction was conducted in the same manner as in Example 1 except that only the catalyst 1 was filled in the reactor tube so as to form a catalyst layer having a length of 3,000 mm. The nitrate bath temperature was high from the start of the reaction and the acrylic acid yield was low. The nitrate bath temperature was increased in order to keep the acrolein conversion at a desired level, in which case the temperature of the nitrate bath increased in a short time. The results of the reaction are shown in Table 3.

Comparative Example 2

A reaction was started in the same manner as in Example 1 except that only the catalyst 2 was filled in the reactor tube so as to form a catalyst layer having a length of 3,000 mm. However, since the temperature of hot spots of the catalyst layer exceeded 400° C. and the reaction became unstable, the reaction had to be stopped.

Comparative Example 3

A reaction was conducted in the same manner as in Example 2 except that only the catalyst 3 was filled in the reactor tube so as to form a catalyst layer having a length of 3,000 mm. The results of the reaction are shown in Table 3.

Comparative Example 4

A reaction was started in the same manner as in Example 2 except that only the catalyst 4 was filled in the reactor tube so as to form a catalyst layer having a length of 3,000 mm. However, since the temperature of hot spots of the catalyst layer exceeded 400° C. and the reaction became unstable, the reaction had to be stopped.

TABLE 3

| Comparative Example | Reaction time (hr) | Temp. of nitrate bath (°C.) | Maximum temperatures of catalyst layers (°C.) | | | Acrolein conversion (mole %) | Acrylic acid yield (mole %) |
|---|---|---|---|---|---|---|---|
| | | | 1st layer | 2nd layer | 3rd layer | | |
| 1 | Initial | 265 | 330 | — | — | 98.0 | 90.5 |
| | 2,000 | 270 | 332 | — | — | 98.5 | 91.0 |
| | 8,000 | 280 | 340 | — | — | 97.3 | 89.9 |
| 3 | Initial | 260 | 328 | — | — | 97.5 | 90.5 |
| | 2,000 | 265 | 330 | — | — | 98.0 | 91.5 |
| | 8,000 | 275 | 335 | — | — | 97.0 | 90.2 |

EXAMPLE 3

A ring-shaped catalyst 5 of 6 mm (outer diameter)×2 mm (inner diameter)×6 mm (length) and a ring-shaped catalyst 6 of 5 mm (outer catalyst)×2 mm (inner catalyst)×5 mm (length) were obtained in the same manner as in Example 1 except that antimony trioxide and titanium dioxide were used as the raw material for antimony and the raw material for titanium, respectively. These catalysts had the following composition when oxygen was excluded.

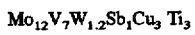

$Mo_{12}V_7W_{1.2}Sb_1Cu_3Ti_3$

These catalysts were filled in a stainless steel-made reactor tube of 20 mm in inner diameter, heated in a molten nitrate bath, in such a manner that the catalyst 5 was closer to the raw material gas inlet of the tube and formed a layer of 800-mm length and the catalyst 6 was downstream of the catalyst 5 and formed a layer of 2,200-mm length. Then, into the tube was introduced a raw material gas having the following composition, at a space velocity (SV) of 2,000 hr$^{-1}$.

| | |
|---|---|
| Acrolein | 12% by volume |
| Oxygen | 14% by volume |
| Steam | 21% by volume |
| Inert gas (e.g. nitrogen) | 53% by volume |

The shapes, volumes and volume ratio of the catalysts 5 and 6 used in the reaction are shown in Table 1, and the results of the reaction are shown in Table 4.

EXAMPLE 4

A ring-shaped catalyst 7 of 12 mm (outer diameter), 4 mm (inner diameter)×12 mm (length), a ring-shaped catalyst 8 of 8 mm (outer diameter)×2 mm (inner diameter)×8 mm (length) and a ring-shaped catalyst 9 of 5 mm (outer diameter)×2 mm (inner diameter)×5 mm (length) were produced in the same manner as in Example 1 except that ferric nitrate, barium nitrate and cerium oxide were used as the raw material for iron, the raw material for barium and the raw material for cerium, respectively. These catalysts were filled into a stainless steel-made reactor tube of 30 mm in inner diameter, heated in a molten nitrate bath, in such a manner that the catalyst 7 was closest to the raw material gas inlet of the reactor tube and formed a catalyst layer of 1,000-mm length, the catalyst 8 was downstream of the catalyst 7 and formed a catalyst layer of 1,000-mm length and the catalyst 9 was downstream of the catalyst 8 and formed a catalyst layer of 1,000-mm length. A reaction was conducted under the same reaction conditions as in Example 3. The shapes, volumes and volume ratios of the catalysts 7, 8 and 9 used in the reaction are shown in Table 1, and the results of the reaction are shown in Table 4.

Incidentally, the catalysts 7, 8 and 9 had the following composition when oxygen was excluded.

$Mo_{12}V_6W_{0.5}Fe_{2.5}Ba_{0.5}Ce_2$

EXAMPLE 5

A spherical catalyst 10 of 10 mm in diameter and a spherical catalyst 11 of 3.5 mm in diameter were obtained in the same manner as in Example 2 except that zirconium oxide and calcium hydroxide were used as the raw material for zirconium and the raw material for calcium, respectively. These catalysts had the following composition when oxygen and carrier were excluded.

$Mo_{12}V_6W_{1.5}Cu_2Zr_{1.5}Ca_{0.5}$

These catalysts were filled in a stainless steel-made reactor tube of 25 mm in inner diameter, heated in a molten nitrate bath, in such a manner that the catalyst 10 was closer to the raw material gas inlet of the tube and formed a layer of 1,200-mm length and the catalyst 11 was downstream of the catalyst 10 and formed a layer of 1,800-mm length. Then, into the tube was introduced, as a raw material gas, a gas having the following composition (obtained by catalytic gas-phase oxidation of propylene in the presence of a molybdenum-bismuth type catalyst) at a space velocity (SV) of 2,000 hr$^{-1}$.

| | |
|---|---|
| Acrolein | 8% by volume |
| Oxygen | 10% by volume |
| Steam | 20% by volume |
| Unreacted propylene and by-produced organic compounds | 2% by volume |
| Inert gas (e.g. nitrogen) | 60% by volume |

The shapes, volumes and volume ratio of the catalysts 10 and 11 used in the reaction are shown in Table 1, and the results of the reaction are shown in Table 4.

TABLE 4

| Example | Reaction time (hr) | Temp. of nitrate bath (°C.) | Maximum temperatures of catalyst layers (°C.) | | | Acrolein conversion (mole %) | Acrylic acid yield (mole %) |
|---|---|---|---|---|---|---|---|
| | | | 1st layer | 2nd layer | 3rd layer | | |
| 3 | Initial | 250 | 325 | 320 | — | 99.4 | 94.3 |
| | 2,000 | 250 | 321 | 318 | — | 99.3 | 94.1 |
| | 8,000 | 255 | 328 | 325 | — | 99.4 | 94.2 |
| 4 | Initial | 245 | 313 | 314 | 314 | 99.0 | 94.0 |
| | 2,000 | 246 | 313 | 315 | 314 | 99.2 | 94.1 |
| | 8,000 | 250 | 318 | 319 | 319 | 99.2 | 94.0 |
| 5 | Initial | 250 | 303 | 320 | — | 99.4 | 93.8 |
| | 2,000 | 253 | 303 | 321 | — | 99.3 | 93.7 |
| | 8,000 | 260 | 305 | 318 | — | 99.2 | 93.9 |

Comparative Example 5

A spherical catalyst 12 of 6 mm in diameter and a spherical catalyst 13 of 8 mm in diameter were obtained in the same manner as in Example 2 except that magnesium oxide was used as the raw material for magnesium. A ring-shaped catalyst 14 of 6 mm (outer diameter)×2 mm (inner diameter)×4 mm (length) was obtained in the same manner as in Example 1 except that tin oxide and titanium dioxide were used as the raw material for tin and the raw material for titanium, respectively.

The catalysts 12 and 13 had the following composition when oxygen and carrier were excluded.

$Mo_{12}V_6W_2Cu_{1.5}Mg_{0.1}$

The catalyst 14 had the following composition when oxygen was excluded.

$Mo_{12}V_4W_2Sn_{0.5}Cu_2Ti_2$

A reaction was conducted under the same conditions as in Example 1 except that only the catalyst 12 was filled in the reactor tube so as to form a catalyst layer of 3,000-mm length. Also, a reaction was conducted under the same conditions as in Example 1 except that only the catalyst 14 was filled in the reactor tube so as to form a catalyst layer of 3,000-mm length. In each case, the temperature of the catalyst layer was high and there was a fear of run-away; therefore, it was impossible to continue the reaction. Further, a reaction was conducted under the same conditions as in Example 1 except that only the catalyst 13 was filled in the reactor tube so as to form a catalyst layer of 3,000-mm length. In this case, the reaction started with no problem but, at the fifth day from the start of the reaction, the acrolein conversion was only 97.5 mole % and the acrylic acid yield was only 89.5 mole % under the conditions of 270° C. (reaction temperature) and 330° C. (maximum catalyst temperature).

EXAMPLE 6

When a reaction was conducted in the same manner as in Example 1 except that the catalyst 13 was filled closer to the raw material gas inlet of the tube so as to form a catalyst layer of 1,000-mm length and the catalyst 14 was filled closer to the raw material gas outlet of the tube so as to form a catalyst layer of 2,000-mm length, the reaction started with no problem and, at the fifth day from the start of the reaction, the acrolein conversion was 99.5 mole % and the acrylic acid yield was 94.5 mole % under the conditions of 252° C. (reaction temperature) and 305° C. (maximum catalyst temperature). In this case, the volume ratio of the catalyst 13 to the catalyst 14 was 4.7/1.

Comparative Example 6

A catalyst 15 whose active component except oxygen had the following composition, was produced in the same manner as in Example 2 except that spherical α-alumina of 6 mm in diameter was used as the carrier. Incidentally, the heat-treatment temperature employed in catalyst production was 400° C.

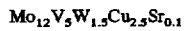

$Mo_{12}V_5W_{1.5}Cu_{2.5}Sr_{0.1}$

Then, an oxidation reaction was conducted in the same manner as in Example 1 except that only the catalyst 15 was used in place of the catalyst 1 and the catalyst 2. However, the temperature of the hot spots of the catalyst layer exceeded 380° C. and the reaction could not be continued and was stopped.

A catalyst 16 was produced in the same manner as for the catalyst 15 except that the heat-treatment temperature employed in catalyst production was changed to 420° C.

Then, an oxidation reaction was conducted in the same manner as in Example 1 except that the catalyst 15 and the catalyst 16 were used in place of the catalyst 1 and the catalyst 2 and that the catalyst 16 was filled in the reactor tube closer to the raw material gas inlet of the tube so as to form a catalyst layer of 500-mm length and the catalyst 15 was filled downstream of the catalyst 16 so as to form a catalyst layer of 1,500-mm length. Although the temperature of the hot spots of the catalyst layers was as low as 340° C., the acrolein conversion was 99.7 mole % and the acrylic acid yield was 89.0 mole %.

EXAMPLE 7

A catalyst 17 was produced in the same manner as for the catalyst 16 except that spherical α-alumina of 8 mm in diameter was used as the carrier. Then, an oxidation reaction was conducted in the same manner as in Example 1 except that the catalyst 15 and the catalyst 17 were used in place of the catalyst 1 and the catalyst 2 and that the catalyst 17 was filled in the reactor tube closer to the raw material gas inlet of the tube so as to form a catalyst layer of 500-mm length and the catalyst 15 was filled downstream of the catalyst 17 so as to form a catalyst layer of 1,500-mm length. As a result, the temperature of the hot spots of the catalyst layers was as low as 300° C., and the acrolein conversion was 99.4 mole % and the acrylic acid yield was 94.2 mole %. Incidentally, the volume ratio of the catalyst 17 to the catalyst 15 was 2.4/1.

What is claimed is:

1. A process for producing acrylic acid by subjecting acrolein or an acrolein-containing gas to gas-phase catalytic oxidation with molecular oxygen or a molecular oxygen-containing gas in a fixed bed multi-tubular reactor, in which process two or more kinds of catalyst particles of different volumes are filled in each reactor tube so as to form a plurality of catalyst layers in the axial direction of the tube in such a manner that the volume of catalyst particle becomes smaller as the position of catalyst layer changes from the raw material gas inlet side of the tube to the raw material gas outlet side, each catalyst particle comprising, as the active component, a compound oxide represented by the following general formula:

$Mo_aV_bW_cA_dB_eC_fD_gO_h$ wherein Mo is molybdenum; V is vanadium; W is tungsten; A is at least one element selected from antimony and tin; B is at least one element selected form copper and iron; C is at least one element selected from magnesium, calcium, strontium and barium; D is at least one element selected from titanium, zirconium and cerium; and O is oxygen; a, b, c, d, e, f, g and h represent the atom numbers of Mo, V, W, A, B, C, D and O, respectively; and when a is 12, $2 \leq b \leq 14$, $0 \leq c \leq 12$, $0 \leq d \leq 5$, $0 < e \leq 6$, $0 \leq f \leq 3$, $0 \leq g \leq 10$, and h is a value determined by the oxidation states of the elements other than oxygen.

2. A process according to claim 1, wherein the ratio of the volume of catalyst particle filled in one catalyst layer to the volume of catalyst particle filled in the following catalyst layer downstream of the former catalyst layer is 1.2/1 to 27/1.

* * * * *